United States Patent [19]

Lynch

[11] Patent Number: 5,285,794
[45] Date of Patent: Feb. 15, 1994

[54] RESPIRATORY GAS MONITOR

[75] Inventor: Thomas J. Lynch, West Chester, Pa.

[73] Assignee: Temple University of the Commonwealth System of Higher Education, Philadelphia, Pa.

[21] Appl. No.: 990,203

[22] Filed: Dec. 14, 1992

[51] Int. Cl.$^5$ ............................................. A61B 5/083
[52] U.S. Cl. ..................................... 128/719; 128/730
[58] Field of Search ........... 128/716, 718.19, 724–730; 73/23.3

[56] References Cited

U.S. PATENT DOCUMENTS

| | | | |
|---|---|---|---|
| 4,211,239 | 7/1980 | Raemer et al. | 128/716 |
| 4,233,842 | 11/1980 | Raemer et al. | 128/719 X |
| 4,359,057 | 11/1982 | Manzella | 128/718 |
| 4,370,986 | 2/1983 | Gebhart et al. | 128/716 |
| 4,413,632 | 11/1983 | Schlessinger et al. | 128/716 |
| 4,619,269 | 10/1986 | Cutler et al. | 128/719 |
| 4,671,297 | 6/1987 | Schulze, Jr. | 128/716 |
| 4,753,245 | 6/1988 | Gedeon | 128/718 |
| 4,763,664 | 8/1988 | Merlainen | 128/719 X |
| 4,856,531 | 8/1989 | Meriläinen | 128/719 |
| 4,917,108 | 4/1990 | Mault | 128/718 |
| 5,046,491 | 9/1991 | Derrick | 128/716 X |
| 5,193,551 | 3/1993 | Pilipski | 128/716 |

Primary Examiner—Angela D. Sykes
Attorney, Agent, or Firm—Seidel, Gonda, Lavorgna & Monaco

[57] ABSTRACT

A method and apparatus for monitoring the respiratory gas of a patient includes an adjustable volume gas mixing chamber which allows for the differences in lung capacity of patients from neonate to adult. A constant flow of a therapeutic gas mixture is measured by a flow meter in a supply line leading to a face mask breathing device. The mask is by-pass connected to the supply line such that the patient inspires from and exhales into the flow from the supply line. Both by-pass and expired gas mix and enter the adjustable-volume chamber, which contains an internal fan and sensors for detecting percentage content of oxygen and carbon dioxide. The chamber is adjusted to a volume where the sensor readings become stable rather than pulsatile. The change in percentages of oxygen and carbon dioxide content in the chamber, as compared to the content in the supply gas, is then entirely due to total-body consumption and production. Whole body rates can be determined by multiplying the percentage change by the flow rate in the supply line.

15 Claims, 2 Drawing Sheets

RESPIRATORY GAS MONITOR

REFERENCE TO GOVERNMENT GRANT

The invention described herein was supported in part by the U.S. Department of Health and Human Services, through Public Health Service grant 5 RO1 DA05998-02.

FIELD OF THE INVENTION

This invention is related to the general field of monitoring respiratory gases; it is particularly related to monitoring and displaying the average whole-body oxygen consumption, and/or carbon dioxide production, and/or the Respiratory Exchange Ratio (RER).

BACKGROUND OF THE INVENTION

Gas monitors are frequently used in conjunction with respirators in intensive care units, particularly in the case of premature infants suffering from respiratory distress syndrome. A medical staff's ability to evaluate a neonate's oxidative status, and to detect any status change during respiratory therapy, would be significantly assisted by a monitor which measures and displays the patient's whole-body oxygen consumption rate and carbon dioxide production rate. Knowledge of the whole-body oxygen consumption rate enables the staff to determine whether the gas mixture supplied through the respirator contains the proper quantity of oxygen. Consumed oxygen and expired $CO_2$ measurements are also used to calculate metabolic rate, Respiratory Exchange Ratio (RER) and cardiovascular function.

DESCRIPTION OF RELATED ART

A respiratory gas monitor for monitoring carbon dioxide output, oxygen consumption and respiratory quotient is described in U.S. Pat. No. 4,856,531 (Merilainen). As described in that patent, such monitors face the problem of combining gas content analysis with an appropriate flow metering. Instrumentation is available which is capable of relatively instantaneous determination of the percentage content of oxygen or carbon dioxide in a gas sample, but measuring the percentage content of an expired gas does not alone indicate the volume of the gas consumed or produced per unit time. Other measurements, such as the volume flow rate of the gas, tidal volume, and the frequency of respiratory cycles are used to calculate or estimate whole-body consumption and production rates.

For example, the apparatus disclosed in Merilainen collects all of the expired gas into a 5-liter mixing chamber. The composition of the mixed gas approximates an average composition of expired gas over the previous ten respiratory cycles (5 liters approximating ten adult respiratory cycles). Each entering expiration forces an equivalent volume of mixed gas from the chamber, thus producing a gas sample of time-averaged content at the current respiratory frequency and in a current respiratory volume. These respiratory-equivalent samples are then diluted in a T-element with a known constant flow rate of ambient air. By assuming that the dilution of the expired gas in the ambient air is proportional to the two flow-rates, one of which is constant, the device displays an approximation of carbon dioxide output by comparing the percentage $CO_2$ content of the gas in the mixing chamber with that of the diluted gas in the outlet hose. The device samples oxygen dilution in the same manner and compares it to the percentage oxygen content in the respirator's supply gas to approximate consumed $O_2$.

Another respiratory gas monitor of the prior art, U.S. Pat. No. 4,619,269 (Cutler et al.), uses a two-way valve to isolate the expired respiratory gas from the background flow of the main ventilation stream, then measures the volume of expired gas with a flow meter and compares its oxygen and carbon dioxide percentages to that of an essentially equal volume sample of the respirator's supply gas.

SUMMARY OF THE INVENTION

An object of the present invention is to provide a compact, simplified respiratory gas monitor which uses less hardware than conventional monitors, and in particular that does not require directional valves or other means to isolate the expired respiratory gas from the supply flow. It should further give accurate readings whether used with neonates, infants, children or adults, despite the significant differences in lung capacity.

The respiratory gas monitor of the present invention accomplishes these objects by providing a constant flow of a therapeutic gas mixture, measured by a flowmeter in a supply line, to a face mask breathing device. The mask is connected to the supply line by a simple T-valve attachment such that the patient may inspire from and exhale into the supply flow. The flow rate is adjusted to a continuous by-pass flow; that is, the by-pass flow decreases temporarily, but is not interrupted, during inspiration. Both by-pass and expired gas enter an adjustable-volume mixing chamber, which contains an internal fan for rapid mixing and sensors for detecting the percentage content of oxygen and of carbon dioxide. The chamber is adjusted to a volume at which the sensor readings become essentially stable rather than pulsatile. The change in percentages of oxygen and carbon dioxide content in the chamber, as compared to the content in the supply gas, is then entirely due to total-body consumption and production, and the respective consumption and production rates can be determined by multiplying the percentage change by the flow rate in the supply line The multiplication can be done to the electrical signals of the sensor outputs, by digital or analog electronics means, and the resulting product displayed by digital read-out or on a calibrated time recorder.

The volume of the gas mixing chamber is adjustable to allow for the differences in respiratory capacity (tidal volume) of patients, i.e., neonates, infants, children or adults. Thus, the user may adjust the volume of the gas mixing chamber to the extent that pulsations of the gas content readings caused by inhalation/expiration are barely discernable. This allows the operator to observe the respiratory frequency, while enabling the apparatus to obtain an accurate and relatively contemporaneous reading of the average oxygen consumption and carbon dioxide production rates regardless of the patient's lung capacity.

In a preferred embodiment, the adjustable volume mixing chamber is defined by a hollow cylindrical tube enclosing a piston-plunger moveable within the tube to increase or decrease the chamber volume. The body of the tube is preferably transparent and has indicator markings to select known volumes by aligning the visible piston face with a marker line.

Other objects, advantages and novel features of the present invention will become apparent from the following detailed description of the invention when considered in conjunction with the accompanying drawings.

BRIEF DESCRIPTION OF THE DRAWINGS

For the purpose of illustrating the invention, there is shown in the drawings a form which is presently preferred; it being understood, however, that this invention is not limited to the precise arrangements and instrumentalities shown.

DESCRIPTION OF THE PREFERRED EMBODIMENT

Figure 1:
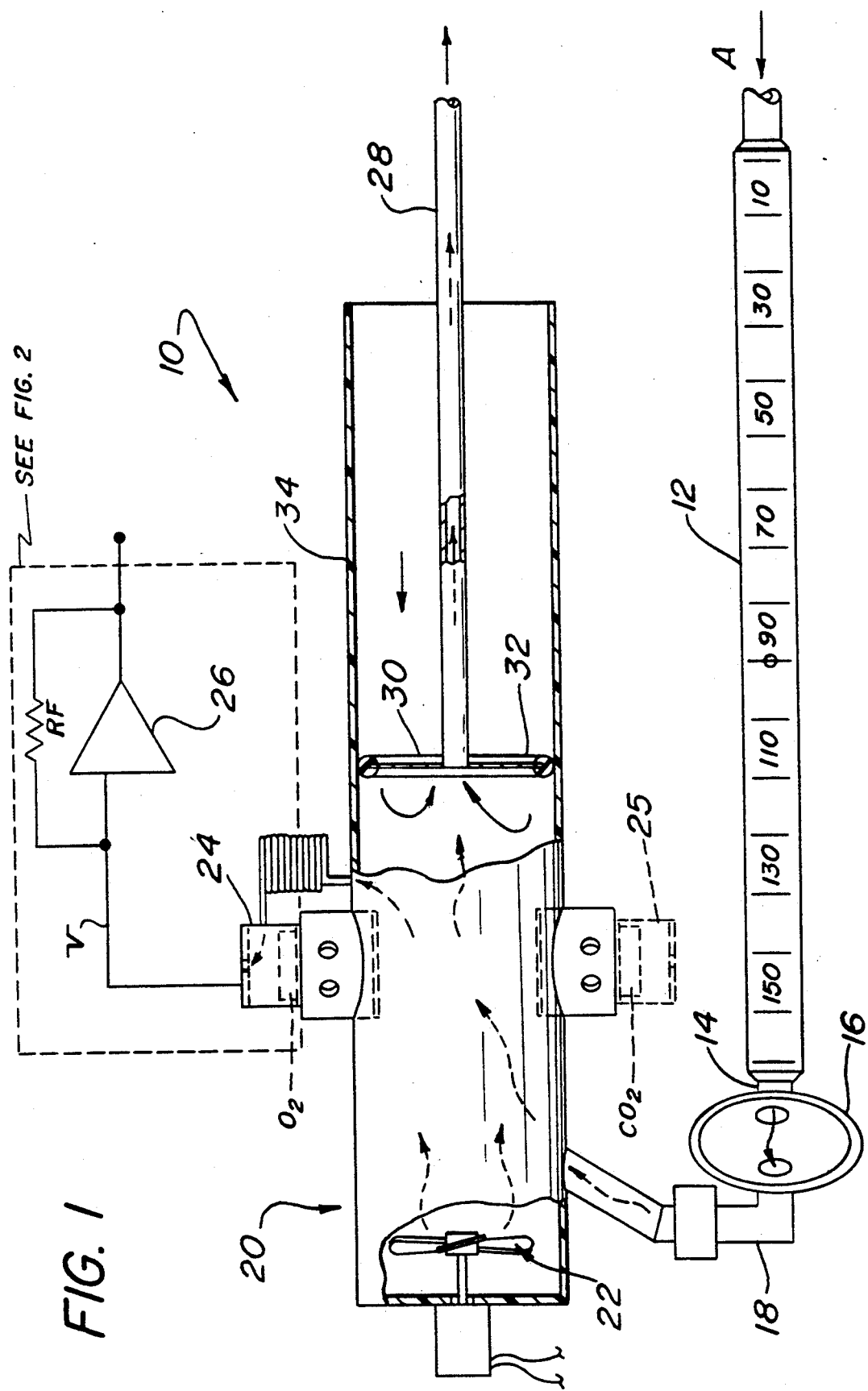
FIG. 1 is a schematic diagram of the respiratory gas monitor of the invention, with a detailed section view of the adjustable volume mixing chamber.

FIG. 1 schematically illustrates the basic design of the respiratory gas monitor 10. A therapeutic gas mixture is supplied at input A and passes through a flow measuring device, such as flowmeter 12, in a supply line 14. The supply line is connected to a face mask 16 configured to fit over the patient's nose and mouth. The supply line is connected to the mask by means, such as a T-coupling (not depicted), by which the respiratory gas may flow past the mask (by-pass gas) or a portion of gas flow be inspired through the mask to the patient during inhalation, and which allows the mask to supply and to receive the respiratory gas expired from the patient, The patient's expired respiratory gas passes back through the mask to be transported with the by-pass gas in tube 18 to a mixing chamber 20.

Provided the flow rate of the supplied gas is kept greater than the patient's intake rate during the inspiratory portion of his respiratory cycle, gas will pass through flowmeter 12 at a steady rate determined by a regulator (not depicted) on the supply tank or respirator control panel. A patient's inspiration flow rate depends on his tidal volume multiplied by his respiratory rate; consequently, the supply tank regulator is adjusted for the size and physical condition of the patient to set a supply flow rate which is greater than his inspiration rate. The higher flow rate of the supplied gas prevents the gas expired by the patient from flowing back into the flowmeter, and also prevents the patient from reinspiring any significant amount.

In some prior art respirators, a directional valve or a set of valves are associated with the face mask to prevent expired gases from reentering the supply line. In the present monitor, as stated above, it has been found that the valve is unnecessary if the therapeutic gas flows at a steady and slightly greater rate than the rate at which the patient can inspire the gas.

The expired respiratory gas is transported with the by-passed therapeutic gas mixture to an adjustable volume gas mixing chamber 20. The chamber 20 includes a circulating device, such as a small electric-powered fan 22, an outlet to an oxygen sensor 24 and an outlet to a carbon dioxide sensor 25, further described below.

As known to those in the art, a mixing chamber may be used to combine gas mixtures received from separate streams, or to equilibrate an accumulation of a single stream of gas having a changing composition. In doing the latter, it acts as a time-averaging device. Although its output flow will follow the same rate characteristic as the input flow, the composition of the mixed gas exiting the chamber will be an averaged composition of the gases received in the chamber during a preceding time interval proportional to the chamber volume. The accuracy of the averaging is also dependent upon the degree of homogeneity achieved by the mixing.

Since the chamber's output is a time-averaged composition, its contemporaneous accuracy in representing the patient's real-time oxidative state is related to the number of respiratory cycles being averaged, and therefore to the volume of the chamber. For example, if the volume of the mixing chamber were such that the mixed gas was representative of the time-averaged composition of the previous ten respiratory cycles, sudden changes in oxidative state might be discernable only after an unacceptable time lag. A mixing chamber having a fixed volume selected to optimize mixing, time-averaging and response time for an adult patient might therefor be inappropriate for the reduced tidal volume and supply flow rate of a neonate (and vice versa).

Consequently, the mixing chamber 20 is adapted to have an adjustable volume. Chamber 20 is formed by a hollow transparent tube 34, such as a tube made of Plexiglas. The volume of the gas mixing chamber 20 is adjusted by moving an enclosed piston 30. The piston has a center bore to which outlet tube 28 is connected in the manner of a hollow piston rod. The piston also has an O-ring gasket 32 on its circumference to seal against the inner wall of the tube 34, forming an air-tight seal between the circumference edge of the piston 30 and the interior surface of the tube 34. The piston 30 can be slid inside the tube 34 to form a chamber volume to suit any patient's lung capacity. Graduated volume indicator lines (not depicted) may be printed on the tube 34 to assist volume adjustments by aligning the piston with a volume indicator line.

A mixing fan 22 inside the chamber rapidly equilibrates the incoming bypass and expired respiratory gases, and aids in venting the gases from the mixing chamber via tube 28. The fan 22 is preferably located at the end of the tube 34 opposite the piston 30. The bypass/respiratory flow tube 28 is preferably located near the fan, and the sensors 24, 25 located toward the piston. Tube 28 is preferably a rigid hollow rod having sufficient length that it protrudes from tube 34, and it may be used to move the piston manually to a particular calibration volume by pushing or pulling.

The objective in moving the piston 30 is to alter chamber volume to attain a balance between competing considerations. Faster system response to changes in gas content are achieved by using a smaller gas mixing chamber volume, but if the volume is too small, the sensors readings will oscillate excessively due to the pulsatile flow pattern of the respiratory cycle. A very large chamber volume would ensure complete mixing and ample time-averaging, resulting in a steady readable sensor display, but have a slow response time to changes. An adjustable volume chamber allows selection of an effective volume for both considerations.

For example, in the depicted embodiment, the cylinder 34 is 5 cm. in diameter and 35 cm. in length, and the chamber 20 volume can be adjusted between approximately 250 to 650 ml. This range accommodates the respiratory frequency and tidal volume of adults to yield a sufficiently rapid response without excessive sensor fluctuation, yet is adjustable to the lower volume to achieve the same response with a much smaller neonatal patient.

In practice, the adjustment can easily be made by reducing the volume until periodic fluctuation of the sensor indicators is clearly discernable on the display or chart recorder as the patient's respiratory cycle, then increasing volume until such fluctuation is just barely discernable. Alternatively, the volume could be set by aligning the piston-plunger 30 with one of the indicator markings on the tube 34 associated with a patient's size, and checking the sensor display to see that no excessive fluctuation is apparent. Should a change in respiratory rate at any time cause excessively fluctuating readings, the volume can be increased by moving the piston until the fluctuation is again just discernable. Such volume adjustment will not effect the calibration of the sensors, since the flow rate out of the chamber does not change with its volume.

Though not described here, the piston 30 could, if desired, be actuated electronically.

The oxygen sensor 24 may be any suitable device for sensing the percentage concentration of $O_2$, such as a micro-fuel type sensor Type B3 manufactured by Teledyne Analytics. Since this micro-fuel sensor is temperature sensitive, the heat content of the expired gas can produce wide variations in the sensor's output current that are not related to oxygen content. Although electronic temperature compensation is likely possible through thermistor feedback to the fuel cell amplifier, it is less complex to merely cool the gas flowing to the sensor back to a temperature near the ambient temperature of the room. Since intensive care areas are usually climate controlled within a relative tight temperature range slight variations of ambient temperature will not be detrimented to the calibrated output current of the micro-fuel sensor.

To achieve cooling to ambient temperature, the oxygen sensor 24 is insulated from the chamber 20 by a hollow, ported platform 23. The flow sample of mixed gas from the chamber is passed through a thin, metal-tubing coil 21 enroute to the sensor 24. The coil 21 allows the sample flow to cool to room ambient temperature by exchanging heat through the metal walls to the ambient atmosphere, while the platform 23 prevents heat conduction from the surface of the chamber 20 to the sensor 24.

The carbon dioxide sensor 25 may be of a temperature sensitive type as the oxygen sensor 24, and require that the sample flow of gas from the mixing chamber be cooled as described above. If it is not temperature sensitive, either by electronic temperature compensation or by the type of sensor itself, the gas sample may flow directly from the interior of the chamber 20 to the sensor 25.

Figure 2:
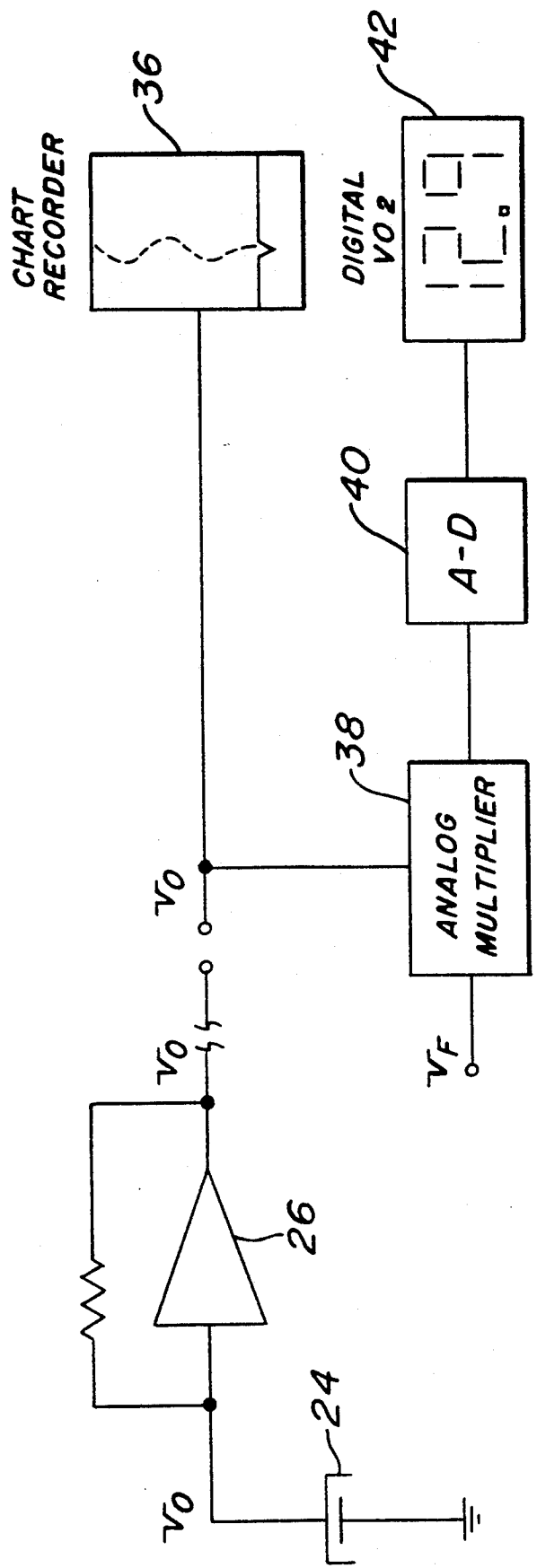
FIG. 2 is a schematic diagram of $O_2$ consumption circuitry which may be used in the practice of the invention.

The output current from the oxygen sensor 24 creates an electrical signal v which is input to oxygen consumption calculation circuitry (shown in FIG. 2) via operational amplifier 26. The oxygen sensor 24 and operational amplifier 26 are selected to be approximately linear over the range of anticipated oxygen levels. A sensor display device, such as device 42 to be described below, may then be calibrated for a particular mixture of supply gas and respond to the collective output voltage of amplifier 26 to display the decrement ($\Delta O_2\%$) in oxygen percentage in the gas mixing chamber as compared to its percentage in the supply mixture.

The display device may be calibrated using a linear (slope-intercept) calibration equation:

$$\%O_{2out} = mv_o + b \qquad \text{Eq. 1}$$

where $v_o$ is the collective output voltage of amplifier 26, m is a proportionality factor (slope) and b is a constant. These quantities m and b are taken into account in the response characteristics of the amplifier 26 and included in the feedback element RF arranged across amplifier 26. The values of m and b included in the response of amplifier 26 indicated by the above calibration equation may be easily determined by exposing the oxygen sensor 24 to two gases of known oxygen content and reading the amplifier 26 output voltage $v_o$ resulting from each exposure. Because the oxygen sensor 24 and amplifier 26 are linear in the anticipated range, the values that m and b contribute to the display device will remain constant. Such display device can then be calibrated for an operating range of $v_o$ to indicate a percentage decrease of oxygen relative to a normal supply mixture.

As an example, if the amplifier 26 is adjusted to output 0.05v when the oxygen sensor is exposed to nitrogen ($\%O_{2out}$ is 0), Equation 1 becomes $\%O_{2out} = 0 = 0.05m + b$. If the oxygen sensor is then exposed to a normal mixture of therapeutic air ($\%O_2$ is 20.9%) and the output of the amplifier $v_o$ is 5.7v, the constants m and b of Equation 1 can be calculated as m = 3.69 and b = −0.185. The calibration equation for the device is then:

$$\%O_{2out} = 3.69v_o - 0.185 \qquad \text{Eq. 1}a$$

If a small amount of $O_2$ is consumed by the patient, such that the oxygen sensor is now exposed to a lower percentage of $O_2$, i.e., lower than that of the normal mixture being supplied, $v_o$ may decrease to, for example, 5.55 volts. Substituting 5.5 volts for $v_o$ in equation 1$a$ gives the new $\%O_{2out}$ as 20.34%. A display device can then be calibrated for an operating range of $v_o$ from 5.7 v down to perhaps 5.2 v to indicate a percentage decrease of oxygen relative to the normal supply mixture.

For example, the decrease in $v_o$ below 5.7 v could be displayed on an analog chart recorder 36 by using $v_o$ to control the stylus. The mark on the chart at any instant would reflect the average instantaneous oxygen consumed by the patient, respiratory frequency would be apparent from regular minor fluctuation, and significant changes over time would be apparent from displacement of the stylus line.

If the device is to be used with a therapeutic gas source in which the oxygen content can be increased by mixing pure oxygen into the standard mixture, a signal proportional to the increase of oxygen in the source gas could be compared to $v_o$ and the difference used in a display device.

To display a digital read-out of total body oxygen consumption ($VO_2$) in milliliters of oxygen per minute, $v_o$ can be further processed using analog multiplier circuitry 38 and an A/D converter 40.

The equation for digitally displaying total body oxygen consumption is similar to the Fick equation for determining consumption of any substance from the circulatory system by a body organ:

$$C_x = F_d([X_a] - [X_v]). \qquad \text{Eq. 2}$$

The Fick equation postulates that the consumption ($C_x$) of a substance (X) by a bodily organ is the difference between arterial [$X_a$] and venous [$X_v$] concentrations of the substance multiplied by the arterial blood flow to the organ ($F_a$). Here, the analogous organ is the whole body, the arterial concentration [$X_a$] is the percentage of oxygen (%$O_2$) in the supplied gas, the venous concentration $[X_v]$ is the percentage of oxygen (%$O_2$) in the bypass/respiratory gas detected by the oxygen sensor, the arterial blood flow $F_a$ is analogous to the flow rate (F) of the supplied gas, and the consumption of a substance $(C_x)$ is the whole-body oxygen consumption ($VO_2$):

$$VO_2 = F([\%O_{2in}] - [\%O_{2out}]) \qquad \text{Eq. 3}$$

or $$VO_2 = F(\Delta\%O_2) \qquad \text{Eq. 3a}$$

Thus, digital display of $VO_2$ could be accomplished by analog multiplication of $v_o$ by a signal $v_f$ proportional to constant flow F, with the resulting product signal input to analog-to-digital converter 40, and its digital equivalent displayed on a digital display device 42.

Although only the $O_2$ calculation circuitry has been described in detail, one with ordinary skill in the art would be able to relate the above description of the $O_2$ calculation circuitry to $CO_2$ calculation and display, and to RER, which is the ratio of $CO_2$ production to $O_2$ consumption. The interconnection for such $CO_2$ circuitry is shown on FIG. 1.

Referring back to FIG. 1, in the set-up and operation of the monitor, the hollow piston 30 is positioned at an approximate volume graduation of the gas mixing chamber 20 depending on the lung capacity of the patient to be monitored. The face mask is placed over the mouth and nose of the patient, and the therapeutic gas supply regulator is adjusted, via flowmeter 12, to flow gas to the patient at a slightly greater rate than the rate at which the patient can inspire. The mixing chamber volume adjustment is then made until periodic fluctuation of the sensor indicators is just discernable on the display or chart recorder as the patient's respiratory cycle.

The present invention may be embodied in other specific forms without departing from the spirit or essential attributes thereof and, accordingly, reference should be made to the appended claims, rather than to the foregoing specification, as indicating the scope of the invention.

What is claimed is:

1. An apparatus for monitoring respiratory gas comprising:
   a measuring means for measuring the volume flow rate of a therapeutic gas supplied to said apparatus;
   a breathing device for supplying a portion of the flow of the therapeutic gas to a patient and for receiving respiratory gas expired from said patient;
   a gas mixing chamber associated with the breathing device and adapted to receive the flow of therapeutic gas and expired respiratory gas and to equilibrate said gasses to an essentially homogenous mixture, wherein the mixing chamber further comprises structure adjusting the chamber volume;
   at least one sensor associated with said gas mixing chamber said sensor sensing the percentage concentration of a gaseous compound in the gas mixture contained within the chamber; and
   means for displaying the difference between percentage concentration of the compound in the mixing chamber to the percentage in the therapeutic gas.

2. An apparatus as in claim 1, wherein said at least one sensor is an oxygen sensor which produces an electrical signal representative of the sensed percentage concentration of oxygen, and wherein the apparatus further comprises means responsive to said signal and to the volume flow rate of the therapeutic gas for deriving a second signal representative of the oxygen consumed per unit time by said patient.

3. An apparatus as defined in claim 2, wherein another sensor is a carbon dioxide sensor which produces an electrical signal representative of the sensed percentage concentration of carbon dioxide, and wherein the apparatus further comprises means responsive to said signal representative of carbon dioxide and to the volume flow rate of the therapeutic gas for deriving a third signal representative of the carbon dioxide produced per unit time by said patient.

4. An apparatus as defined in claim 3, wherein the apparatus further comprises means responsive to said second and third signals for displaying the Respiratory Exchange Ratio of said patient.

5. An apparatus as in claim 2, wherein said structure for adjusting the volume of the gas mixing chamber includes at least one wall of the chamber being moveable toward and away from an opposite wall and having a moveable sealing contact with its surrounding walls.

6. An apparatus as in claim 5, wherein said mixing chamber is defined by a hollow cylindrical tube having one fixed end wall and an opposite end wall defined by a piston moveable within the tube.

7. An apparatus as in claim 6, wherein said gas mixing chamber includes a fan facilitating the mixing of the respiratory gas and therapeutic gas.

8. An apparatus as in claim 1, wherein said structure for adjusting the volume of the gas mixing chamber includes at least one wall of the chamber being moveable toward and away from an opposite wall and having a moveable sealing contact with its surrounding walls.

9. An apparatus as in claim 8, wherein said mixing chamber is defined by a hollow cylindrical tube having one fixed end wall and an opposite end wall defined by a piston moveable within the tube.

10. An apparatus as in claim 9, wherein said gas mixing chamber includes a fan facilitating the mixing of the respiratory gas and therapeutic gas.

11. An apparatus for monitoring respiratory gas comprising:
   a measuring means for measuring the volume flow rate of a flow of therapeutic gas supplied to said apparatus;
   a gas mixing chamber adapted to receive the flow of therapeutic gas and expired respiratory gas and to equilibrate said gasses to an essentially homogenous mixture, sand mixing chamber further comprising structure adjusting chamber volume;
   a pneumatic line connected to a breathing device and to the gas mixing chamber for conveying the flow of therapeutic gas through the breathing device to the gas mixing chamber;
   the breathing device adapted to allow the patient to inspire a portion of the flow of the therapeutic gas and to expire respiratory gas back into the pneumatic line;
   a fan associated with the mixing chamber facilitating the mixing of the respiratory gas and therapeutic gas mixture; and
   at least one sensor associated with said gas mixing chamber which produces an electrical signal representative of a sensed percentage concentration of a gaseous compound in the gas mixture contained within the chamber.

12. An apparatus as defined in claim 11, wherein the structure for adjusting the volume of the gas mixing chamber includes at least one wall of the chamber being moveable toward and away from an opposite wall and having a moveable sealing contact with its surrounding walls.

13. An apparatus as in claim 12, wherein said mixing chamber is defined by a hollow cylindrical tube having one fixed end wall and an opposite end wall defined by a piston moveable within the tube.

14. A method for monitoring respiratory gas comprising the steps of:

supplying a steady flow of therapeutic gas to a patient breathing device at a volume flow rate greater than the volume flow rate of the inspiration portion of the patient's respiratory cycle;

measuring the volume flow rate of the therapeutic gas prior to the breathing device;

passing the therapeutic gas supplied to the breathing device uninhibitedly through the breathing device to a gas mixing chamber having adjustable volume, such that the patient may inspire a portion of the flow during the inspiration portion of the breathing cycle without interrupting the flow of the remaining portion to the mixing chamber;

passing the patient's expired respiratory gas back through the breathing device to be carried with the therapeutic gas to the mixing chamber;

mixing the therapeutic and respiratory gasses in the chamber to an essentially homogenous mixture;

sensing the concentration of a gaseous substance in the essentially homogenous mixture, adjusting the volume of said mixing chamber to control sensor response time necessary to detect changes in the concentration of a gaseous substance in the mixing chamber;

comparing said concentration to the concentration of the same substance in the therapeutic gas to detect changes in the concentration caused by the patient's respiratory exchange.

15. A method for monitoring respiratory gas as in claim 14, further comprising the step of:

multiplying the detected change by the measured volume flow rate of the therapeutic gas to determine the patient's whole-body consumption or production of the substance in units of volume per unit time.

* * * * *